(12) United States Patent
Duval

(10) Patent No.: US 12,256,894 B2
(45) Date of Patent: Mar. 25, 2025

(54) PORTABLE MEDICAL DEVICES AND SYSTEMS

(71) Applicant: Boston Scientific Scimed, Inc., Maple Grove, MN (US)

(72) Inventor: George Duval, Sudbury, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 726 days.

(21) Appl. No.: 16/951,414

(22) Filed: Nov. 18, 2020

(65) Prior Publication Data

US 2021/0145267 A1 May 20, 2021

Related U.S. Application Data

(60) Provisional application No. 62/937,379, filed on Nov. 19, 2019.

(51) Int. Cl.
| | |
|---|---|
| *A61B 1/00* | (2006.01) |
| *A61B 1/05* | (2006.01) |
| *A61B 1/06* | (2006.01) |
| *A61B 50/31* | (2016.01) |

(52) U.S. Cl.
CPC ...... *A61B 1/00108* (2013.01); *A61B 1/00042* (2022.02); *A61B 1/00045* (2013.01); *A61B 1/00066* (2013.01); *A61B 1/05* (2013.01); *A61B 1/0676* (2013.01); *A61B 50/31* (2016.02); *A61B 2050/311* (2016.02)

(58) Field of Classification Search
CPC ..... A61B 1/0605; A61B 1/0625; A61B 1/063; A61B 1/0638; A61B 1/0655; A61B 1/0676; A61B 1/068; A61B 1/00108; A61B 1/00039–00042; A61B 1/0661
See application file for complete search history.

(56) References Cited

U.S. PATENT DOCUMENTS

| | | | |
|---|---|---|---|
| 6,066,089 A * | 5/2000 | Costello | A61B 1/00048 600/102 |
| 6,692,432 B1 | 2/2004 | Yarush | |
| 7,025,762 B2 | 4/2006 | Johnston | |
| 8,790,253 B2 | 7/2014 | Sunagawa | |
| 2007/0225555 A1 * | 9/2007 | Stefanchik | A61B 17/3415 600/104 |
| 2010/0125165 A1 * | 5/2010 | Torii | A61B 1/233 600/106 |

(Continued)

OTHER PUBLICATIONS

Bae, Jung Kweon et al., Smartphone-Based Endoscope System for Advanced Point-of-Care Diagnostics: Feasibility Study, JMIR Mhealth and Uhealth, Jul. 2017, 5(7):e99 (17 pages).

*Primary Examiner* — Alexandra L Newton
(74) *Attorney, Agent, or Firm* — Bookoff McAndrews, PLLC

(57) ABSTRACT

A medical system may comprise an endoscope, including a handle and a sheath having a first illumination source, a second illumination source, and an imaging device at a distal tip of the sheath. The first illumination source may be configured to emit white light. The second illumination source may be configured to emit a non-white light. The system may also comprise a display device, a controller configured to interface with the endoscope and the display device, and a carrying case configured to contain the endoscope, the display device, and the controller.

10 Claims, 7 Drawing Sheets

(56) References Cited

U.S. PATENT DOCUMENTS

| | | | |
|---|---|---|---|
| 2015/0173592 A1* | 6/2015 | Leeflang | A61B 1/00087 |
| | | | 600/109 |
| 2016/0000300 A1* | 1/2016 | Williams | A61B 1/0676 |
| | | | 600/109 |
| 2018/0084980 A1* | 3/2018 | Watanabe | A61B 1/0655 |
| 2019/0324261 A1* | 10/2019 | Ogawa | G06T 5/002 |

* cited by examiner

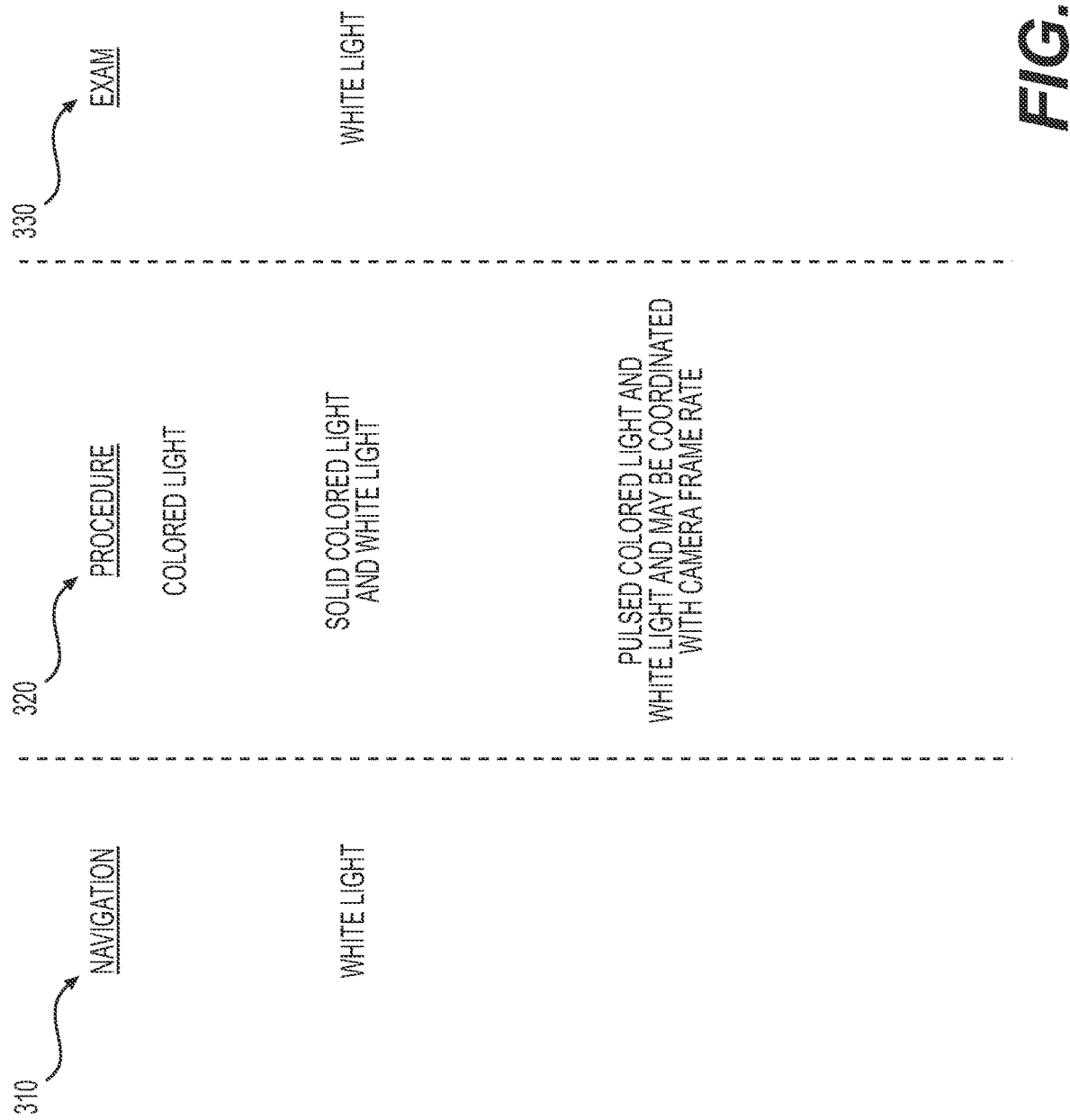

PORTABLE MEDICAL DEVICES AND SYSTEMS

CROSS-REFERENCE TO RELATED APPLICATIONS

This application claims the benefit of priority from U.S. Provisional Application No. 62/937,379, filed on Nov. 19, 2019, which is incorporated by reference herein in its entirety.

TECHNICAL FIELD

The disclosure relates generally to portable medical devices and systems. More specifically, aspects of the disclosure pertain to portable endoscopic devices, which may be adapted for use in performing percutaneous endoscopic procedures (PEG).

BACKGROUND

Endoscopic techniques may be used for a variety of procedures. An endoscope may have a handle portion and an insertion portion. The endoscope may be outfitted with optical devices that may allow an operator to view an environment near a distal tip of the insertion portion. A system for performing an endoscopic procedure may also include display devices for viewing outputs from the optical devices. Endoscopic procedures may be performed in specialized environments, such as endoscopy suites.

However, certain patients who may be in need of an endoscopy procedure may be non-ambulatory or may otherwise be unable to access or have difficulty accessing facilities having endoscopy suites. Therefore, a need exists for portable endoscopy devices or systems.

SUMMARY

Examples of the present disclosure relate to, among other things, portable endoscopy devices or systems. Each of the examples disclosed herein may include one or more of the features described in connection with the disclosed examples.

A medical system may comprise an endoscope, including a handle and a sheath having a first illumination source, a second illumination source, and an imaging device at a distal tip of the sheath. The first illumination source may be configured to emit white light. The second illumination source may be configured to emit a non-white light. The system may also comprise a display device, a controller configured to interface with the endoscope and the display device, and a carrying case configured to contain the endoscope, the display device, and the controller.

Any of the medical systems disclosed herein may include any of the following features. The medical system may further comprise a PEG kit. The carrying case may be configured to contain the PEG kit. The controller may include a first component configured to control the first illumination source and a second component configured to control the second illumination source. The display device may include a tablet device. The controller may be battery-powered. The sheath may further include a third illumination source. The third illumination source may be configured to emit white light. The controller may be configured to enable light emission from the first illumination source independently of light emission from the second illumination source and to enable light emission from the second illumination source independently of light emission from the first illumination source. The controller may be configured to instruct (1) the first illumination source to emit pulsed white light at a first frequency and (2) the second illumination source to emit pulsed non-white light at a second frequency. The first frequency and the second frequency may be such that, while a pulse of white light is emitted from the first light source, a pulse of non-white light is not emitted from the second light source. The first frequency and the second frequency may be such that, while a pulse of non-white light is emitted from the second light source, a pulse of white light is not emitted from the first light source. A frame rate of the imaging device may be such that, while the imaging device is capturing an image, a pulse of white light is emitted. The display device may be mountable on a lid of the carrying case. A working channel may extend longitudinally through the sheath. The sheath may have a diameter between approximately 8 mm and approximately 9 mm. The working channel may have a diameter between approximately 2 mm and approximately 3 mm.

In another example, a medical system may comprise an endoscope, including: a handle; and a sheath having a first illumination source, a second illumination source, and an imaging device at a distal tip of the sheath. The first illumination source may be configured to emit white light. The second illumination source may be configured to emit a non-white light. The medical system may further comprise a first component configured to control the first illumination source, and a second component configured to control the second illumination source. The controller may be configured to enable light emission from the first illumination source independently of light emission from the second illumination source and to enable light emission from the second illumination source independently of light emission from the first illumination source. The medical system may further comprise a carrying case configured to contain the endoscope and the controller.

Any of the medical systems disclosed herein may have any of the following features. The controller may be configured to instruct (1) the first illumination source to emit pulsed white light at a first frequency and (2) the second illumination source to emit pulsed non-white light at a second frequency. The first frequency and the second frequency may be such that, while a pulse of white light is emitted from the first light source, a pulse of non-white light is not emitted from the second light source.

An exemplary medical method may include removing an endoscope from a carrying case; advancing the endoscope into a body lumen of a subject; navigating the endoscope to a location in the body lumen while a first light source at a distal tip of the endoscope emits white light; locating a desired position on a surface of the subject's skin while a second light source at the distal tip of the endoscope emits non-white light; and positioning a PEG device at the desired position.

Any of the medical methods and systems described herein may include any of the following steps or features. When the locating step is performed, (1) the first illumination source may emit pulsed white light at a first frequency and (2) the second illumination source may emit pulsed non-white light at a second frequency. The first frequency and the second frequency may be such that, while the pulse of white light is emitted from the first light source, the pulse of non-white light is not emitted from the second light source. The method may further comprise visualizing the body lumen using a display device that displays an image captured using an imaging device. A frame rate of the imaging device may be such that, while the imaging device is capturing the image, the pulse of white light is emitted.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "distal" refers to a direction away from an operator, and the term "proximal" refers to a direction toward an operator. The term "approximately," or like terms, includes values +/−10% of a stated value.

BRIEF DESCRIPTION OF THE DRAWINGS

The accompanying drawings, which are incorporated in and constitute a part of this specification, illustrate examples of the present disclosure and together with the description, serve to explain the principles of the disclosure.

FIGS. 6 and 7 depict aspects of exemplary medical methods.

DETAILED DESCRIPTION

A portable endoscopy system may include an endoscope, display device(s), controller, and/or accessories, which may be housed together in a case, such as a carrying case. Accessories may include kits for performing procedures (e.g., a PEG kit). The endoscope may have features that are particularly adapted for PEG procedures, including, for example, multiple illumination sources offering different colors of light (e.g., red and white light). The case may be of a size and weight that facilitate carrying the system to remote sites, where subjects may be located (e.g., nursing homes, assisted living facilities, or locations far from medical facilities (e.g., hospitals)).

Figure 1:
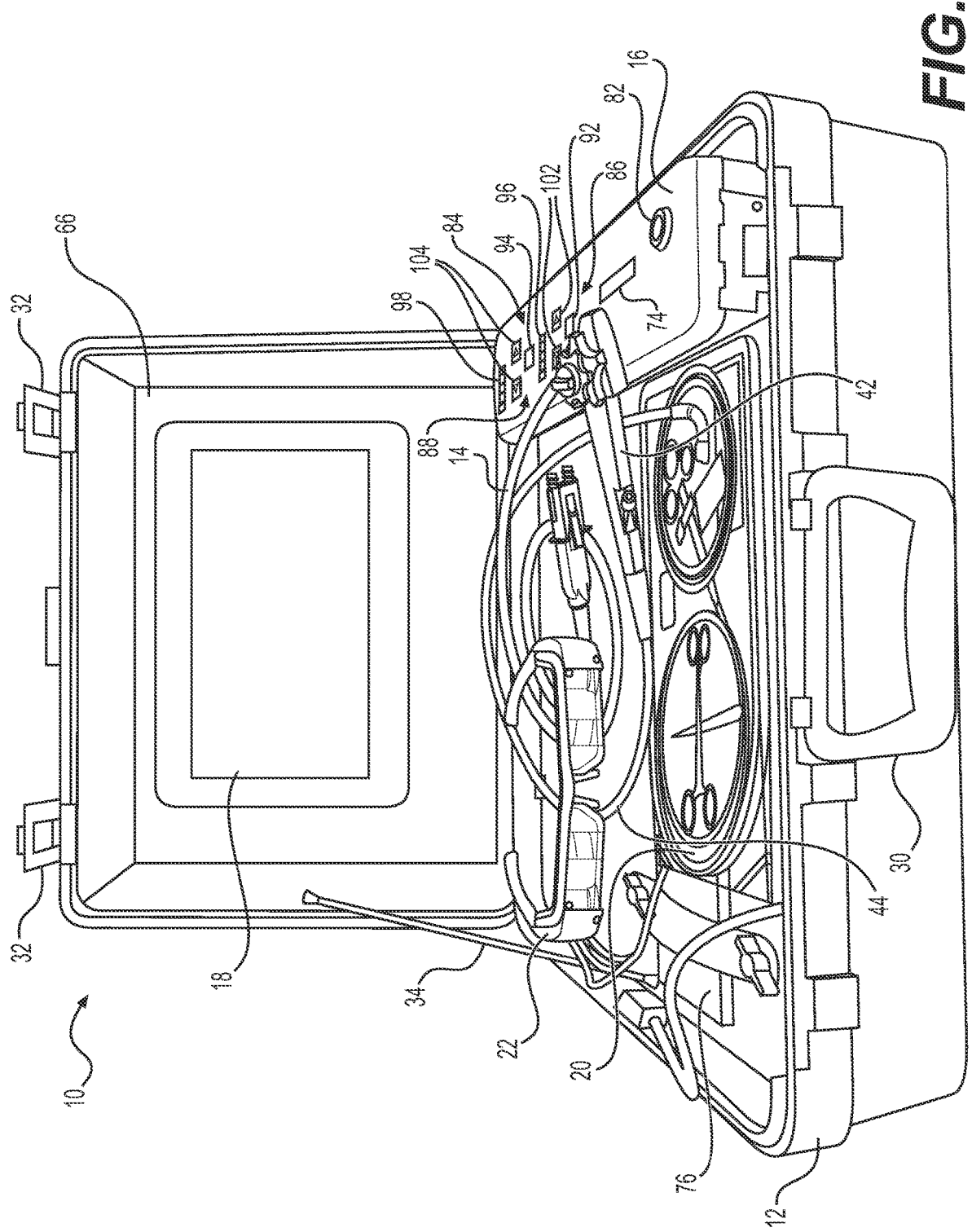
FIG. 1 depicts an exemplary medical system.

FIG. 1 depicts an exemplary system 10. System 10 may include a carrying case 12, which may house the components of system 10. System 10 may further include, for example, an endoscope 14, a controller 16, a display 18, and one or more accessories. For example, accessories can include a PEG kit 20 and a heads-up device 22, which may include smart glasses. Smart glasses may display information on lenses of glasses such that a user can view the information while performing other tasks, without needing to divert attention to a separate display. Heads-up device 22 may also include virtual reality systems. System 10 may be a self-contained system that includes all (or nearly all) of the components necessary for a user to perform a PEG procedure at a bedside. While a PEG procedure is referenced herein, it will be appreciated that the systems and methods described may be used with a wide variety of procedures, including any known or future endoscopic, urologic, bronchoscopic, or the like procedures. For example, the systems and methods described herein may be used in procedures including gastric bypass procedures, gastro-jejunal anastomosis procedures, natural translumenal endoscopic surgery ("NOTES"), or assisted laproscopic procedures. Any of the components of system 10 may be single-use devices. It will be appreciated that the elements of FIG. 1 are not necessarily shown to scale.

Carrying case 12 may be configured to provide storage that is adapted to house the components of system 10. For example, carrying case 12 may include partitions (which may be molded to mate with particular components of the elements of system 10, including endoscope 14), compartments, anchors, straps, or other structures for housing and securing components of system 10. Carrying case 12 may include a handle 30 that may be used to hold and move carrying case 12 between locations. Carrying case 12 may also include closure mechanisms 32 (e.g., latches) and mechanisms to secure carrying case 12 in an open configuration (e.g., a support bar 34, which may be hinged and may include locking features). Carrying case 12 may have hard sides (e.g., rigid plastic sides) or soft sides. Carrying case 12 may have features configured to protect components of system 10 when they are housed within carrying case 12, including shock absorption, protection from water, humidity, etc. Carrying case 12 may also have wheels or other features to facilitate movement of carrying case 12.

Figure 2:
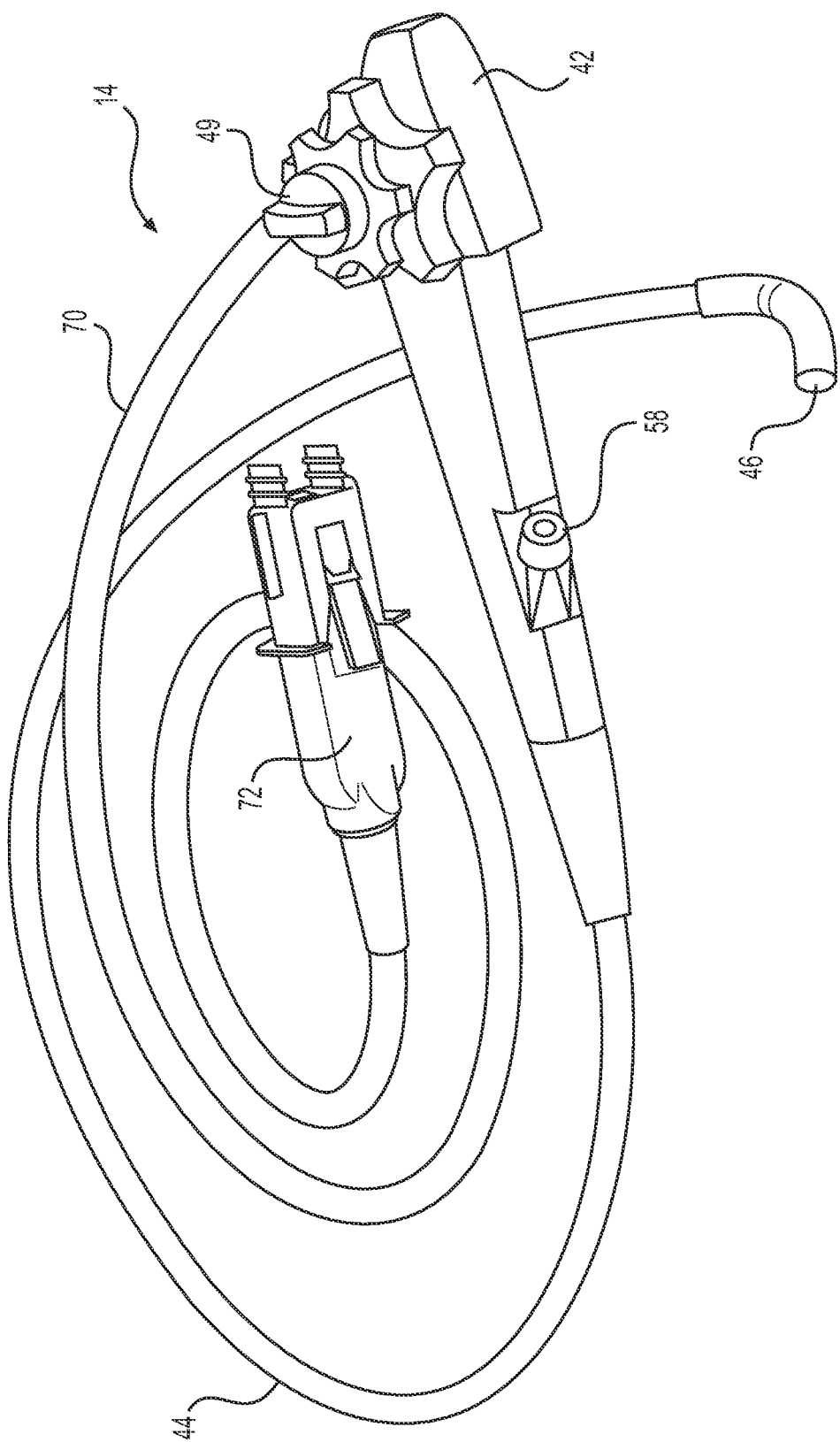
FIG. 2 depicts an endoscope of the medical system depicted in FIG. 1.

As shown in FIG. 2, endoscope 14 may have a handle 42 and a sheath 44. Sheath 44 of endoscope 14 may be configured to be inserted into a body lumen of a subject. For example, sheath 44 may be configured to be inserted into a gastrointestinal (GI) lumen of a patient. Sheath 44 may have a diameter of approximately 8-9 mm, which may facilitate using the scope in subjects outside of a hospital or with subjects that may have narrowed body lumens requiring navigation. Sheath 44 may have a distal tip 46.

Figure 3:
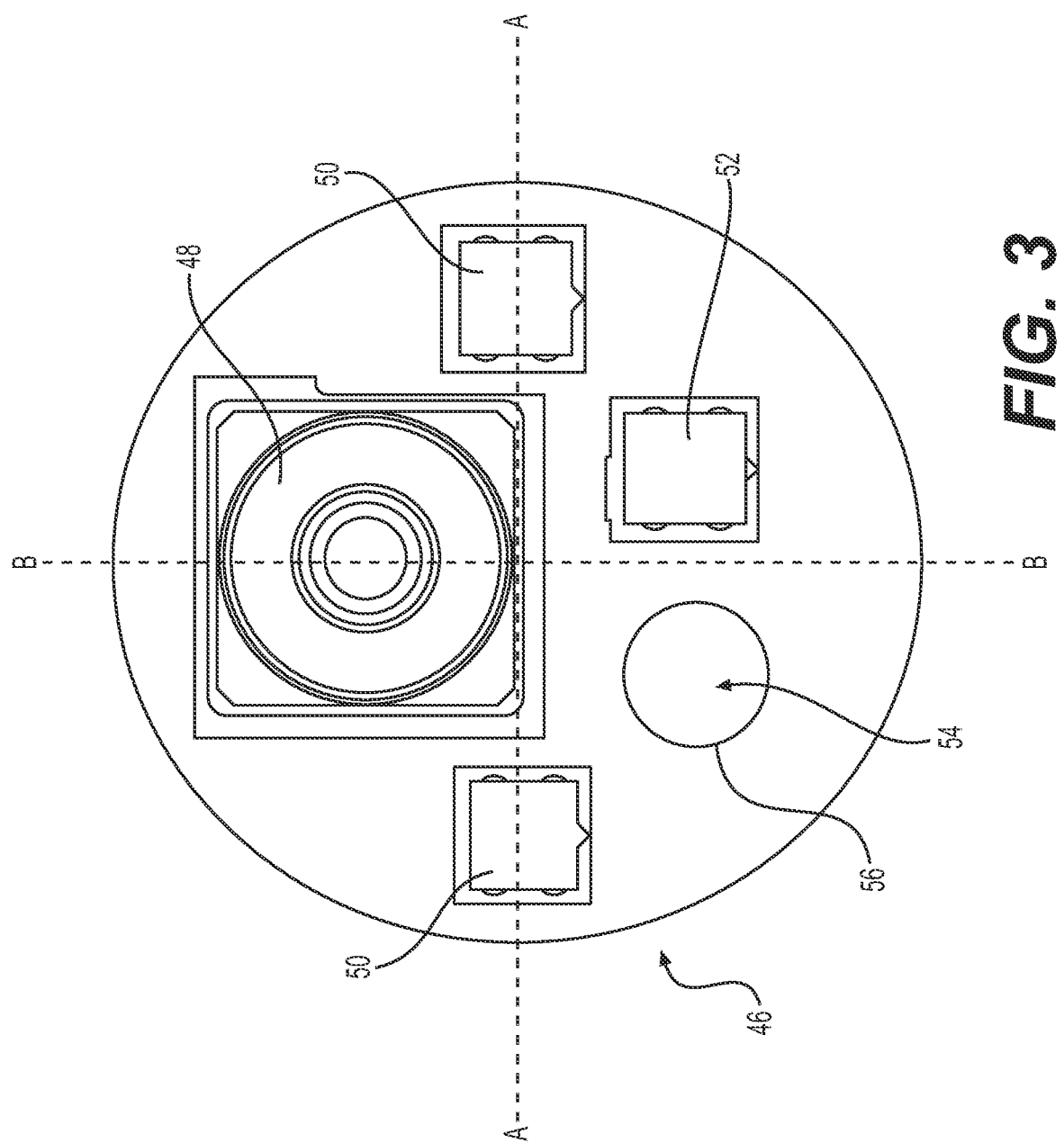
FIG. 3 depicts a distal tip of the endoscope of FIG. 2.

As shown in FIG. 3, distal tip 46 may include an imaging device 48. Imaging device 48 may be forward facing along a longitudinal axis of sheath 44. Alternatively, imaging device 48 may be side-facing or may face an angle. Imaging device 48 may include a camera, an optical fiber, and/or another mechanism for transmitting an image from distal tip 46 to display 18. Further details regarding connections between scope 14 and display 18 will be discussed below.

A working channel 54 may extend longitudinally through sheath 44, from handle 42 to distal tip 46. Working channel 54 may terminate distally in an opening 56 at distal tip 46. Working channel 54 may include a separate tube extending through sheath 44 (not shown) or may be integrally formed from sheath 44. A proximal end of working channel 54 may be accessed via handle 42 using, e.g., a port 58. Working channel 54 may have a width of 2-3 mm, which may be smaller than other types of endoscopes. The size of working channel 54 may be adapted for use with a PEG procedure, as described below. A relatively small size of working channel 54 may facilitate a relatively smaller cross-sectional size of sheath 44. Although endoscopes are referred to herein, it will be appreciated that the scope of the disclosure also encompasses devices including, for example, colonoscopes, ureteroscopes, bronchoscopes, duodenoscopes, or any other like sheaths, catheters, or tubes useful for medical procedures.

With reference to FIG. 2, sheath 44 may be steerable using controls 49 in handle 42. For example, sheath 44 may include articulation wires (not shown) that enable distal tip 46 to be articulated in one or more directions. For example, distal tip 46 may be steerable along 180 degrees or 360 degrees. Any suitable mechanism may be used to facilitate steering sheath 44. As shown in FIG. 2, for example, controls 49 may include knobs.

Referring again to FIG. 3, distal tip 46 may also include one or more white illumination sources 50, and one or more colored illumination sources 52. Colored illumination source 52 may be, for example, red or green. Illumination sources 50, 52 may include, for example, light emitting diodes (LEDs) or light fibers that may transmit light from a proximal light source. Illumination sources 50, 52 may be individually controlled, as described in further detail below. For example, only white light may be emitted from illumination source(s) 50, only colored (e.g., red or green) light may be emitted from illumination source(s) 52, or both white light and colored light may be emitted from light sources 50 and 52 simultaneously. Although distal tip 46 is show as having one colored illumination source 52 and two white illumination sources 50, different numbers of illumination sources (colored or white) may be used. Alternatively (not shown), distal tip 46 may include multiple light sources of different colors (e.g., LEDs) that may be combined to form white light. In such an alternative example, the multiple colored lights may be independently controllable so that white or colored light may be emitted, and distal tip may have multiple LEDs of the same color so that light of that color may be formed simultaneously with white light. Colored illumination sources 52 may also be disposed on a second, separate sheath or catheter.

As shown in FIG. 3, white illumination sources 50 may be positioned on, or approximately, on a diameter/cross-sectional axis (labeled "A") of distal face 62 of distal tip 46. A center of imaging device 48 may fall on a first side of diameter A, approximately between white illumination sources 50 on another diameter/cross-sectional axis (labeled "B") of distal face 62. Colored illumination source 52 and working channel 54 may be positioned on a second side of diameter A, opposite the first side. Opening 56 of working channel 54 may be positioned on one side of diameter B, and colored illumination source 52 may be positioned on the other side of diameter B. The configuration of FIG. 3 is merely exemplary, and the components of distal tip 46 may be alternatively arranged. For example, distal tip 46 may employ a side-viewing configuration and may have features such as elevators for manipulating working tools inserted into working channel 54. Although endoscope 14 is described as being used in conjunction with other elements of system 10, it will be appreciated that endoscope 14 may be used alone or in conjunction with only a subset of elements of system 10 (e.g., controller 16, discussed in further detail below).

With reference to FIG. 1, display 18 may be a portable display, such as a tablet computer that may have a touchscreen. Alternatively, display 18 may be another type of display, such as a flat-screen display. Display 18 may be passive or may be interactive. Where display 18 is interactive, display 18 may be controlled via a touchscreen, a control panel, or input devices (e.g., mouse, keyboard, trackpad, mobile device application), etc. Display 18 may integrate features allowing a user to control endoscope 14. Such potential features will be discussed in further detail, below. Display 18 may be a device specialized for use with system 10. Alternatively, display 18 may be a multi-function device, such as a tablet, phone, or other portable electronic device, that may be used for other purposes, as well.

Display 18 may be permanently or detachably housed in a portion of carrying case 12. For example, a lid 66 of carrying case 12 may be configured to receive display 18. Lid 66 may include a molded compartment with surfaces shaped to mate with surfaces of display 18. Display 18 may be in a portion of carrying case 12 via, for example, a snap fit, hook and loop fastener, latches, etc. During travel, display 18 may be housed in one portion of carrying case 12 for protection. Display 18 may be repositioned (e.g., to lid 66) when it is time to perform a procedure with system 10. Alternatively to being housed within carrying case 12 when in use, display 18 may alternatively be placed in an alternative location (e.g., on a table). Display 18 may have features, such as a kickstand, to allow for positioning of display 18 in a desired location. Display 18 may be wired or may be wireless. Display 18 as shown in FIG. 1 is wireless. Carrying case 12 may have inductive or plug-in charging features to charge display 18 or other components of system 10. For example, a battery 76 (discussed in further detail below) may be housed in carrying case 12 and may be used to power display 18. Battery 76 may also function as a junction for operatively connecting one or more of controller 16, display 18, and endoscope 14. Alternatively, another junction between controller 16, display 18, and endoscope 14 may be utilized, or such connections may occur without a separate junction component.

Figure 4:
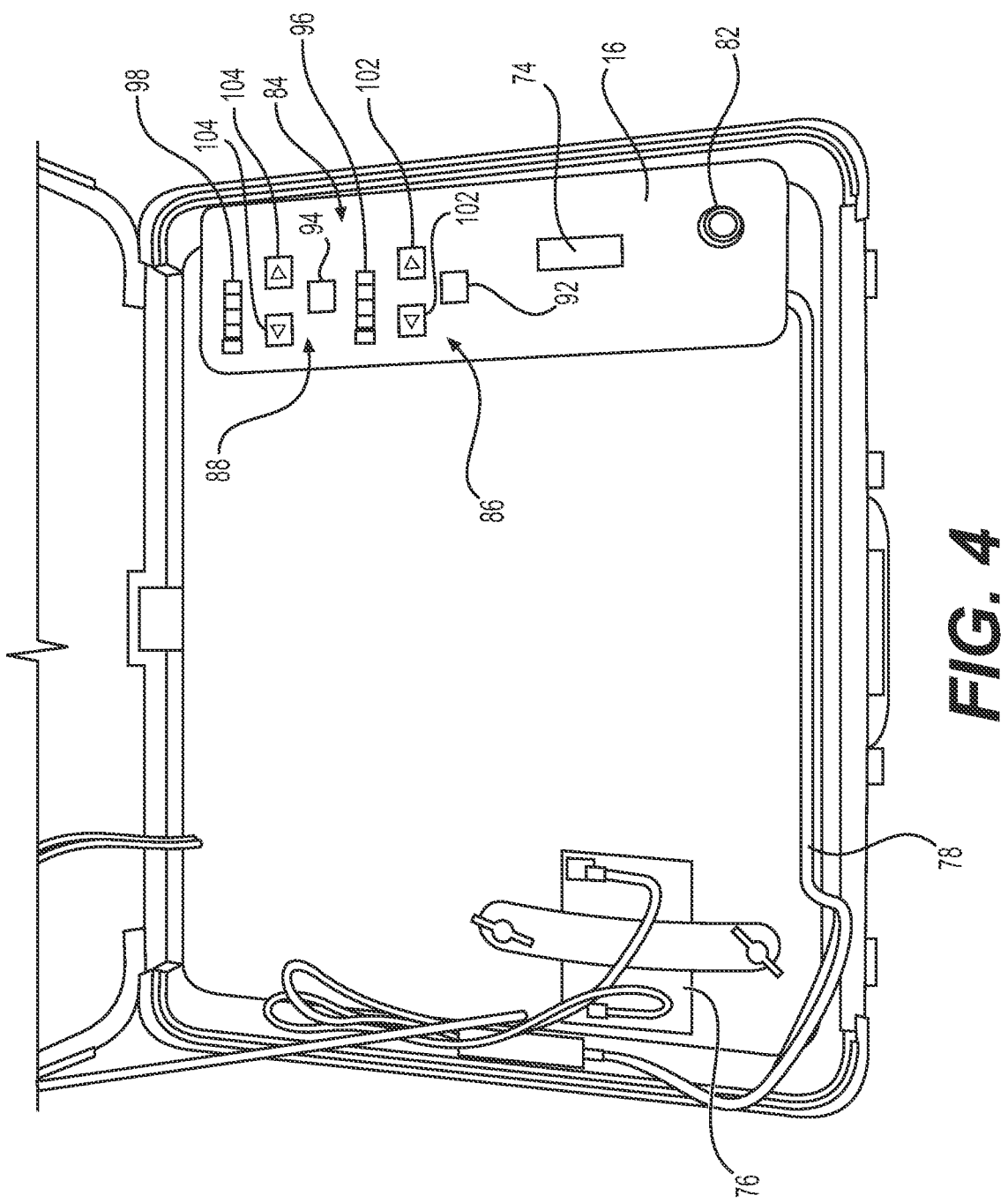
FIG. 4 depicts a carrying case and controller of the exemplary medical system of FIG. 1.

With particular reference to FIG. 4, controller 16 may interface with endoscope 14 and display 18, along with other devices, such as, for example a personal computer, a smart phone, a portable electronic device, a server, or a network (e.g., of a hospital, medical facility, home, or other environment). Although controller 16 is shown as a separate component, it will be appreciated that controller 16 may also be a portion of endoscope 14 or display 18. Connections between controller 16, endoscope 14, and/or display 18 may be wireless or wired connections. In the case of wireless connections, such connections may be made, for example, via Bluetooth or Wi-Fi. A combination of wireless and wired connections may be utilized; for example, one of a connection between controller 16 and endoscope 14 or between controller 16 and display 18 may be wireless, while the other may be wired.

Endoscope 14 may be connected to controller 16 via a cable 70, shown in FIG. 2. Cable 70 may include components that can provide power to imaging device 48 and/or illumination devices 50, 52. Components of cable 70 may also transmit control signals to imaging device 48, as well as images from imaging device 48 to controller 16. Components of cable 70 may facilitate controlling and powering illumination devices 50, 52, which may be controlled separately or together, as discussed in further detail below. In cases in which optical fibers are used, fibers may extend through cable 70. Cable 70 may also include tubing to transmit air, water, and/or suction to or from endoscope 14. Cable 70 may terminate proximally in a connector 72. Connector 72 may be insertable into and may mate with a port 74 (shown in FIG. 4) of controller 16.

With reference to FIG. 4, controller 16 may be battery-powered and/or may include a cord 78 for connecting controller 16 to a power outlet. Where controller 16 is battery-powered, batteries 76 of controller 16 may be rechargeable or disposable. A battery-powered controller 16 may also be used while the battery is being charged using, e.g., a power cord that may simultaneously charge battery 76. A power cord may be stored within carrying case 12. While battery 76 is shown as being external to controller 16, battery 76 may also be formed as a portion of controller 16.

As shown in FIG. 4, controller 16 may have an interface allowing a user to control operations of endoscope 14. It will be appreciated that the controls described herein may alternatively be located on handle 42 of endoscope 14. Controller 16 may include a first mechanism 82, which may have a variety of functions. Mechanism 82 may include any other suitable structure, including a toggle, switch, button, knob, or other structure. For example, mechanism 82 may control power to controller 16 or endoscope 14, aspects of imaging device 48 (e.g., image capture, zoom, mode, etc.), or may have an alternative function.

Controller 16 may also include a lighting interface 84. Lighting interface 84 may include, for example, white light controls 86 and colored light controls 88. White light controls 86 may be operative to control white illumination sources 50. Colored light controls 88 may be operative to control colored illumination sources 52. White light controls 86 and colored light controls 88 may each include a power control 92, 94, respectively. Power controls 92, 94 may be buttons and may illuminate in the same color as the illumination source they pertain to (e.g., power control 92 may illuminate white, while power control 94 may illuminate a color of colored illumination source 52, such as red). Alternatively, power controls 92, 94 may include any suitable structure, including switches, toggles, knobs, or other mechanisms. White light controls 86 and colored light controls 88 may also include illumination level indicators 96, 98, respectively. Illumination level indicators 96, 98, may light up or otherwise indicate a brightness of white illumination source(s) 50 and/or colored illumination source(s) 52. White light controls 86 and colored light controls 88 may further include brightness adjusters 102, 104. As shown in FIG. 4, brightness adjusters 102, 104 may include two buttons that are configured to increase or decrease a brightness of white illumination source(s) 50 or colored illumination source(s) 52. Brightness adjusters 102, 104 may alternatively include any suitable structure, including switches, levers, toggles, knobs, etc., or other numbers of buttons. White light controls 86 and colored light controls 88 may be operative to separately adjust a brightness of white illumination source(s) 50 and colored illumination source(s) 5, respectively 2.

A method of operation of system 10 will be described herein. A user of system 10 may transport system 10 to a site where a procedure is desired to be performed. The user may plug in system 10 or may forego that step if system 10 is battery-powered. The user may open carrying case 12 and may remove endoscope 14 and/or PEG kit 20. The user may also position display 18 (if display 18 is not pre-positioned in carrying case 12) and/or put on heads up device 22. Display 18 may be placed in a position that is convenient for viewing by user 18 during the procedure.

Once a subject has been prepared, endoscope 14 may be advanced through a body lumen of the subject (e.g., through the mouth of the patient and into the GI tract). While endoscope 14 is advanced and positioned, white illumination source(s) 50 may be utilized so that the user of endoscope 14 may visualize the position of distal tip 46 on display 18 using imaging device 48. While endoscope 14 is being positioned, colored illumination source(s) 52 may not be used. Where multiple light colored light sources (e.g. colored LEDs) are used to produce white light instead of a single source of white light, those multiple sources may be combined to produce white light while endoscope 14 is advanced through the body lumen.

Figure 5B:
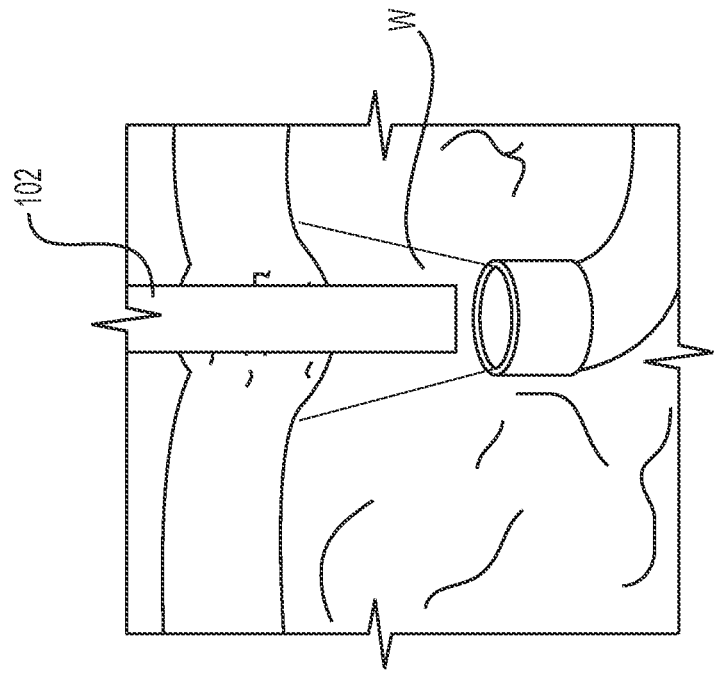
FIGS. 5A-5B depicts an exemplary procedure using the endoscope of FIG. 2.
Figure 5A:
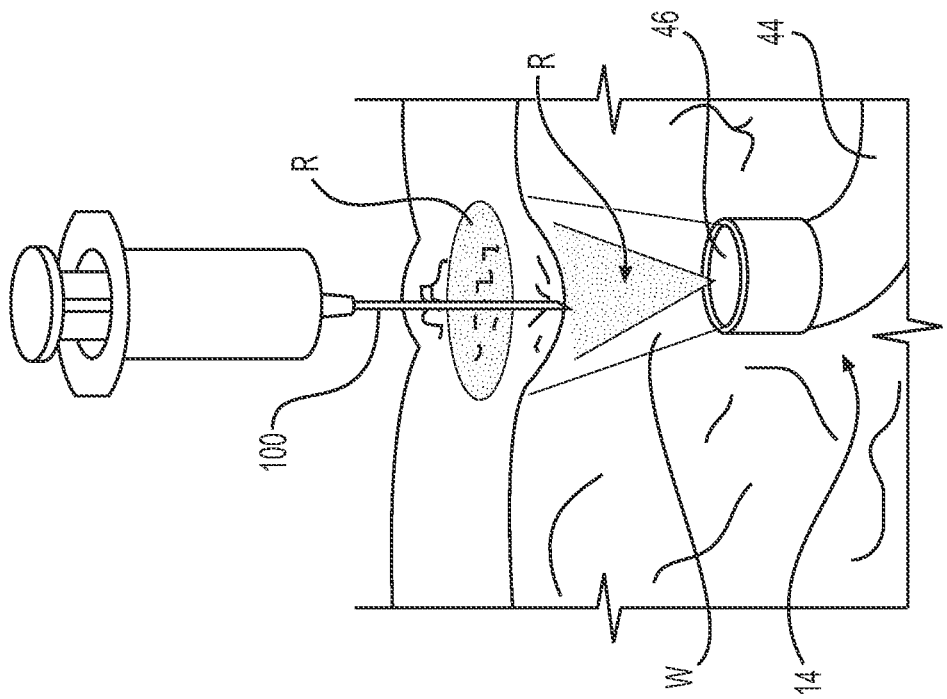

As shown in FIG. 5A, after endoscope 14 has been advanced to the desired location, colored illumination source(s) 52 (not shown in FIG. 5A) may be utilized so as to aid a physician in identifying a location on a surface of a subject's skin where it is desired to pass a PEG tube. For example, colored illumination source(s) 52 may emit red light R, shown in FIG. 5A. As compared to white light, red light may provide better translumination. Red light may more easily pass through the abdominal wall so that it is visible on an external surface of a subject's skin. Alternatively, another color of light, such as green light, may be emitted from colored illumination source(s) 52. White illumination source(s) 50 may be deactivated while colored illumination source(s) 52 is being used to position the PEG tube on an external surface of the subject's skin.

While the PEG tube is being positioned, light may be emitted from both white illumination source(s) 50 and colored illumination source(s) 52, as shown in FIG. 5A. White light W (shown in FIG. 5A) from white illumination source(s) 50 (not shown in FIG. 5A) may enable a user to continue to visualize the body lumen, via imaging device 48. Controller 16 and/or one or both of white illumination source 50 and colored illumination source 52 may be configured so that illumination sources 50, 52 have a duty cycle such that they pulse (turn on and off) at a frequency that is greater than is detectable by the human eye. Controller 16 and/or one or both of white illumination source 50 and colored illumination source 52 may be configured so that the pulsing causes white illumination source 50 and colored illumination source 52 to emit light at alternating times. White illumination source 50 may emit white light while colored illumination source 52 is not emitting light, and vice versa. Cycling of white illumination source 50 and colored illumination source 52 may be coordinated with a frame rate of imaging device 48. For example, while imaging device 48 is capturing images, white illumination source 50 may emit white light. While imaging device 48 is not capturing an image, colored illumination source 52 may emit colored light. Thus, white light from white illumination source 50 and colored light from colored illumination source 52 may both be utilized without light from colored illumination source 52 interfering with visualization via imaging device 48 and without light from white illumination source 50 interfering with a user's utilization of colored light to identify placement for the PEG device on the external surface of the subject's skin. The user may perform a procedure to position/install a PEG tube at the position indicated by the red light.

As shown in FIG. 5A, a user may identify red light R on the surface of a patient's skin and may insert a needle 100 into the location indicated by red light R.

As shown in FIG. 5B, after a PEG tube 102 is positioned, the user may deactivate colored illumination source 52 and activate (or continue using) white illumination source 50 (illumination sources 50, 52 not shown in FIG. 5B) to emit white light W. The user may perform a final examination to ensure that the PEG is properly positioned.

In addition to or in alternative to a PEG procedure, a user may perform exploratory or other procedures. For example, prior to performing a PEG procedure, a user may utilize imaging device 48 and/or a tool inserted in working channel 54 in order to perform an examination or procedure. Such examinations and/or procedures may enable a user to determine whether a subject is in need of further treatment. Furthermore, the techniques identified herein are not limited to the identified system 10 or PEG procedure described herein. For example, the described alternating of colored light and white light, which may be tied to a frame rate of a camera, may be used in a variety of contexts. Such methods are not limited to endoscope 14 or system 10.

Figure 6:
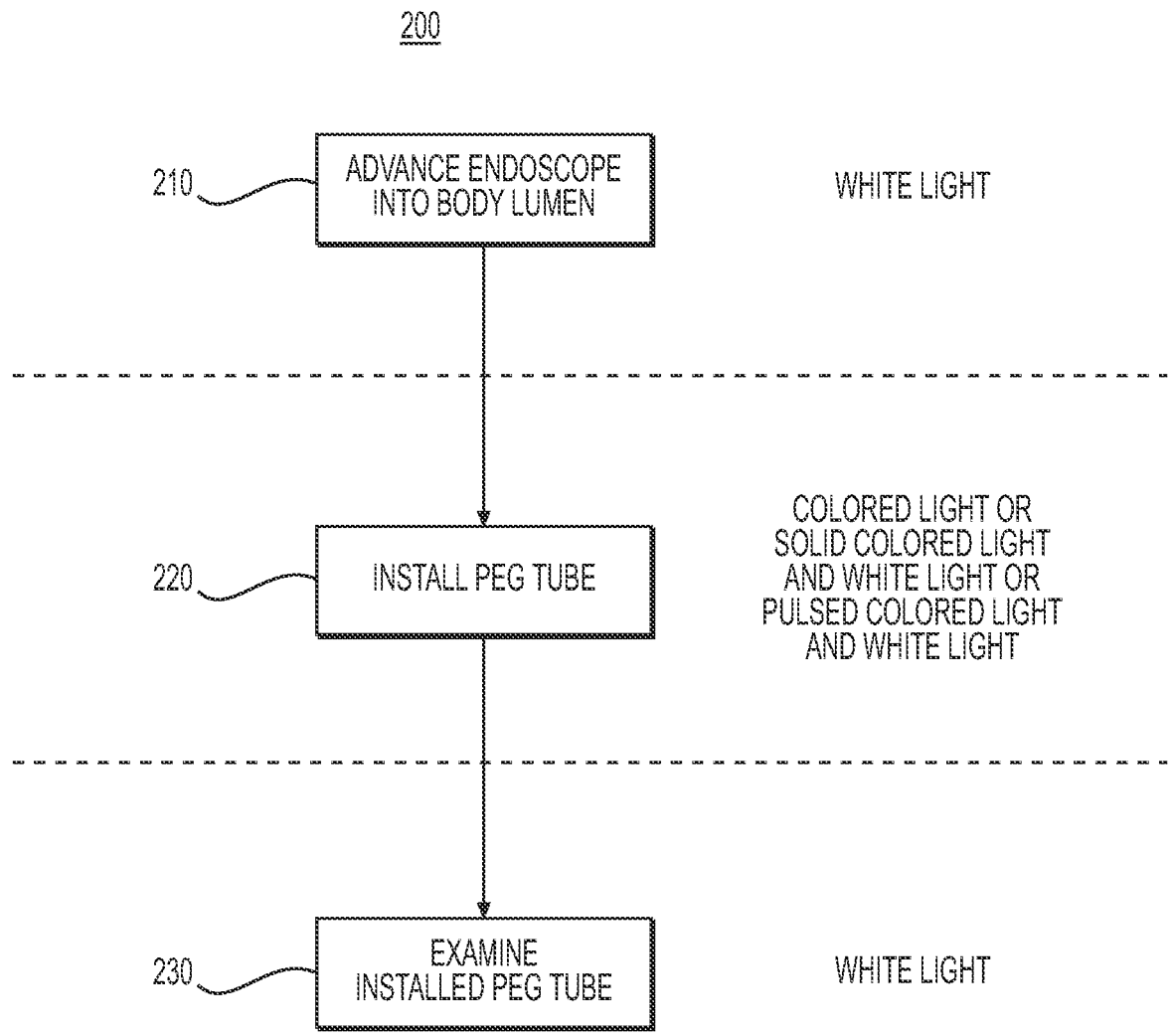

FIGS. 6 and 7 illustrate exemplary medical methods. In method 200 of FIG. 6, in step 210, an endoscope may be advanced into a body lumen. During step 210, white light may be utilized (from, for example, white illumination source 50). In step 220, a PEG tube may be installed. During step 220, colored light (from, for example, colored illumination source 52) may be emitted. Alternatively, solid white light and colored light may be emitted. In a further alternative, pulsed colored light and white light may be emitted, as described above. Such pulsed light may be coordinated with a frame rate of an imaging device, such as imaging device 48. During step 230, an examination of an installed PEG tube may be conducted, and white light may be utilized. During step 230, a user may confirm that the PEG tube has been appropriately placed.

FIG. 7 shows phases of a medical procedure, along with lighting that may be used during the phase. In a navigation phase 310 (which may have any of the features of step 210), white light may be emitted. In a procedure phase 320, colored light (from, for example, colored illumination source 52) may be emitted. Alternatively, solid white light and colored light may be emitted. In a further alternative, pulsed colored light and white light may be emitted, as described above. Such pulsed light may be coordinated with a frame rate of an imaging device, such as imaging device 48. Step 220 is an example of procedure phase 320. However, it will be appreciated that phase 320 encompasses procedures other than PEG tube installation. In examination phase 330, white light may be emitted as a user verifies that a procedure is complete.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

I claim:

1. A medical system comprising:
 an endoscope, including:
  a handle; and
  a sheath having a first illumination source, a second illumination source, and an imaging device at a distal tip of the sheath, wherein the first illumination source is configured to emit white light, and wherein the second illumination source is configured to emit a red light;
 a display device;
 a controller configured to interface with the endoscope and the display device, wherein the controller includes:
  a first control configured to allow a user to control a brightness of the first illumination source;
  a second control configured to allow a user to control a brightness of the second illumination source, wherein the first control and the second control are configured to enable the user to control the brightness of the first illumination source and the brightness of the second illumination source independently of one another; and
 a carrying case configured to contain the endoscope, the display device, and the controller;
 wherein the controller is configured with a duty cycle such that the controller instructs (1) the first illumination source to emit a white light that pulses at a first frequency greater than that detectable by a human eye and (2) the second illumination source to emit a red light that pulses at a second frequency greater than that detectable by the human eye;
 wherein the first frequency and the second frequency are such that, while a pulse of white light is emitted from the first illumination source, a pulse of non-white light is not emitted from the second illumination source, and while the pulse of non-white light is emitted from the second illumination source, the pulse of white light is not emitted from the first illumination source;
 wherein the controller, the first illumination source, and the second illumination source are configured such that the first frequency and the second frequency cause the first illumination source and the second illumination source to emit light at alternating times; and
 wherein a frame rate of the imaging device is such that, while the imaging device is capturing an image, the pulse of white light is emitted, and wherein the imaging device captures images only when the first illumination source is emitting the pulse of white light.

2. The system of claim 1, further comprising a PEG kit, and wherein the carrying case is configured to contain the PEG kit.

3. The system of claim 1, wherein the sheath further includes a third illumination source, wherein the third illumination source is configured to emit white light.

4. The system of claim 1, wherein a working channel extends longitudinally through the sheath.

5. The system of claim 1, wherein the sheath has a diameter between approximately 8 mm and approximately 9 mm, and wherein a working channel has a diameter between approximately 2 mm and approximately 3 mm.

6. The system of claim 1 wherein the controller includes a first power control button configured to enable and disable light emission from the first illumination source independently of light emission from the second illumination source and a second power control button configured to enable or disable light emission from the second illumination source independently of light emission from the first illumination source.

7. The system of claim 1, wherein, while the imaging device is capturing the image, the second illumination source is always disabled.

8. The system of claim 1, wherein the display device includes a first brightness level indicator that indicates the brightness of the first illumination source and a second brightness level indicator indicating the brightness of the second illumination source.

9. The system of claim 1, wherein each of the first control and the second control include two buttons that are configured to increase or decrease the brightness of the first illumination source and the second illumination source.

10. The system of claim 1, wherein each of the first illumination source and the second illumination source include a power control.

* * * * *